US00PP17309P2

(12) United States Plant Patent
Hansen

(10) Patent No.: US PP17,309 P2
(45) Date of Patent: Dec. 26, 2006

(54) ***HOSTA* PLANT NAMED 'PRAIRIE SKY'**

(50) Latin Name: *Hosta hybrida*
Varietal Denomination: Prairie Sky

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 2 days.

(21) Appl. No.: 11/231,167

(22) Filed: Sep. 20, 2005

(51) Int. Cl.
*A01H 5/00* (2006.01)

(52) U.S. Cl. ..... Plt./353

(58) Field of Classification Search ..... Plt./353
See application file for complete search history.

(56) References Cited

PUBLICATIONS http://www.shadyoaks.com/GeneratedItems/Pages/Hosta6.html.*

* cited by examiner

*Primary Examiner*—Wendy Haas
(74) *Attorney, Agent, or Firm*—Penny J. Aguirre

(57) ABSTRACT

A new cultivar of *Hosta* named 'Prairie Sky', that is characterized by its intensely blue foliage with leaves that are heart-shaped, slightly cupped and lightly puckered. 'Prairie Sky' has a vigorous growth habit and blooms in mid July to mid August with pale lavender flowers on erect scapes.

1 Drawing Sheet

Botanical classification: *Hosta hybrida.*
Cultivar designation: 'Prairie Sky'.

BACKGROUND OF THE INVENTION

The present invention, *Hosta* 'Prairie Sky', relates to a new and distinct cultivar of *Hosta*, botanically known as a *Hosta hybrida*, hereinafter referred to as 'Prairie Sky'.

'Prairie Sky' was selected in 2002 and originated from a controlled cross made by the inventor in 1998 in Waseca, Minn. between the pod parent designated '95-56' derived from *Hosta rupifraga*×*Hosta* 'Maruba Iwa' (not patented) and the pollen parent *Hosta* 'Blue Jay' (not patented). 'Prairie Sky' was selected primarily for its intensely blue foliage and vigorous growth habit. 'Prairie Sky' differs from the pollen parent, 'Blue Jay', in that 'Prairie Sky' is a larger plant with larger, more cupped leaves and a more vigorous growth habit.

Asexual reproduction of the new cultivar was first accomplished by the inventor by division in Waseca, Minn. in 2004. Asexual reproduction of the new cultivar by division and tissue culture has shown that the unique features of 'Prairie Sky' are stable and reproduced true to type in successive generations.

SUMMARY OF THE INVENTION

The following traits have been repeatedly observed in trials in Minnesota for a period of six years and represent the characteristics of the new cultivar. These attributes in combination distinguish 'Prairie Sky' as a new and unique cultivar of *Hosta.*

1. The foliage of 'Prairie Sky' is intensely blue and comprised of heart-shaped, slightly cupped and lightly puckered leaves. The leaves of 'Prairie Sky' are particularly blue in the spring.
2. 'Prairie Sky' is a medium sized *Hosta* with a mounded habit.

3. 'Prairie Sky' is a vigorous grower, particularly for a *Hosta* with blue foliage.
4. 'Prairie Sky' blooms in mid July to mid August with pale lavender flowers that are tightly clustered on upright flower scapes.

BRIEF DESCRIPTION OF THE DRAWING

The accompanying colored photograph illustrates the overall appearance and distinct characteristics of the new *Hosta*. The photograph was taken in June of a mature plant of 'Prairie Sky' as grown outdoors in Waseca, Minn. for a period of six years. The colors in the photograph are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of six year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Prairie Sky' is a cultivar of *Hosta hybrida.*

Parentage: Pod parent; proprietary seedling '95-56' (*Hosta rupifraga*×*Hosta* 'Maruba Iwa') (not patented), pollen parent *Hosta* 'Blue Jay' (not patented).

General description:

*Blooming period.*—About 4 weeks, typically from July 15 to August 15 in Minnesota.

*Plant habit.*—Herbaceous perennial, clump forming, mounded habit.

*Height and spread.*—Reaches about 43 cm (17 in) in height and 91 cm (36 in) in width.

*Hardiness.*—U.S.D.A. Zones 3 to 8.

*Culture.*—Light to full shade, moist soils of moderate fertility.

*Diseases and pests.*—No susceptibility or resistance to diseases or other pests has been observed for 'Prairie Sky'.

*Root description.*—Freely branched, fleshy.

*Propagation.*—In vitro propagation is the preferrred method utilizing typical methods for *Hosta*, division are also possible.

*Root development.*—Rooted transplants from tissue culture fully develop in a 96-cell liner in about 6 to 8 weeks in a greenhouse with average temperatures of about 70° F.

*Growth rate.*—Vigorous.

Foliage description:

*Leaf shape.*—Broadly ovate.

*Leaf division.*—Simple.

*Leaf base.*—Cordate.

*Leaf apex.*—Cuspidate.

*Leaf aspect.*—Slightly cupped.

*Leaf venation.*—About 8 to 11 pairs of veins, campylodrome pattern, impressed on upper surface and raised on lower surface, color matches foliage coloration.

*Leaf margins.*—Entire.

*Leaf attachment.*—Petiolate.

*Leaf arrangement.*—Basal, radiate spirally from base.

*Leaf surface.*—Lightly puckered, glaucous on upper and lower surface, spring foliage is more glaucous than summer foliage, lower surfaces are more glaucous than upper surfaces.

*Leaf substance.*—Above average.

*Leaf orientation.*—Held upright on petioles that are upright or up to about a 45° angle to center.

*Leaf color.*—Spring foliage; upper and lower surface N138A with heavy glaucous coating of 191C. Summer foliage; upper surface 137A with glaucous coating of 191A, lower surface 137B with glaucous of 191C.

*Leaf size.*—Average of 18 cm (7 in) in length, average of 15 cm (6 in) in width.

*Leaf quantity.*—About 5 to 7 per shoot (eye).

*Petiole size.*—About 30 cm in length, average 1 cm in width.

*Petiole color.*—Inner surface 144A with glaucous coating of 191C B, outer surface 144A near margins becoming 144D at centers.

*Petiole surface.*—Glaucous, both surfaces.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from vertical.

*Scape size.*—About 46 to 60 cm in length, about 5 mm in width.

*Scape color.*—144B.

*Scape surface.*—Glaucous.

*Leaf bracts.*—About 2, about 3 cm in length and 1.2 cm in width, papery, lanceolate in shape, 158C in color blushed and thin lines of N77C, dry to 162A.

Flower description:

*Inflorescence type.*—Terminal racemes of single tubular-shaped flowers, closely spaced on upper 10 cm of scape.

*Lastingness of inflorescence.*—About 4 weeks from first opening bloom to fading of last opening bloom, individual blooms last about one day.

*Flower shape.*—Tubular.

*Flower number.*—About 25 to 30.

*Flower internode length.*—Up to about 7 mm.

*Flower fragrance.*—None.

*Flower bud shape.*—Spathulate.

*Flower bud size.*—Up to about 3 cm in length and 1 cm in diameter.

*Flower bud color.*—Emerges N155B heavily shaded towards apex with 83C, matures to N155B shaded with 84A prior to opening.

*Flower size.*—About 4 cm in length and about 2 cm in diameter.

*Flower color.*—85C to 85D.

*Pedicels.*—About 7 mm in length and 2 mm in diameter, 196D in color.

*Perianth features.*—Comprised of 6 tepals, 3 interior and 3 exterior, fused in tube region and about one half of expanded region then overlapping towards apex.

*Tepal shape.*—Spatulate.

*Tepal size.*—About 3.5 cm in length, up to 1.3 cm in width.

*Tepal color.*—Outer surface 85C to 85C with shading of 85A, inner surface N155C (whiter) with shading of 85A and 85B.

*Tepal texture.*—Glabrous.

*Floral bracts.*—1 per flower, lanceolate in shape, papery, 158C in color blushed and thin lines of N77C, about 2 cm in length and 8 mm in width.

Reproductive organs:

*Gynoecium.*—1 Pistil. Style is about 4.3 cm in length, 1 mm in width and 155B in color. Stigma is 3-lobed, 155B in color and 0.75 mm in diameter. Ovary is superior, compound, composed of 3 locules, oblong in shape, 5 mm in length, 2 mm in width and 144D in color.

*Androecium.*—6 stamens, filament is 155B in color, about 4 cm in length, 0.7 mm in width, longer than perianth but curved inward, anthers are 3 mm in length, 1.5 mm in width, attachment is versatile, 202A in color, dehiscence is longitudinal, pollen is abundant and 15C in color.

*Fruit.*—Fruit set was not observed under the conditions tested.

I claim:

1. A new and distinct cultivar of *Hosta* plant named 'Prairie Sky' as herein illustrated and described.

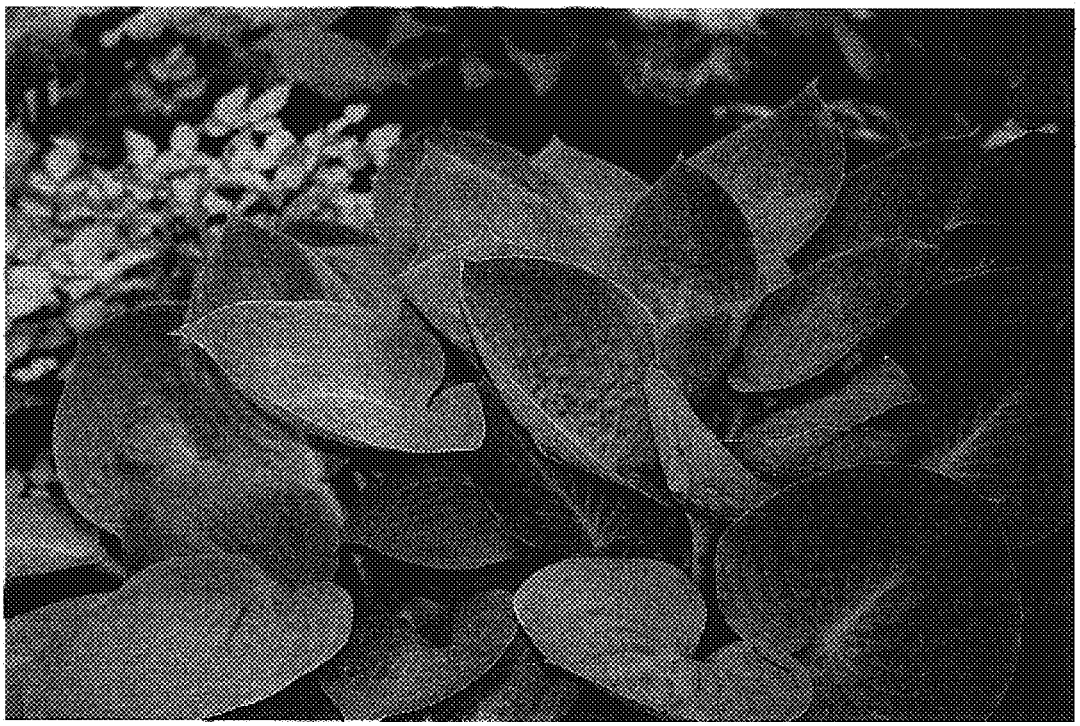

* * * * *